US012797085B2

(12) United States Patent
Papannagari et al.

(10) Patent No.: US 12,797,085 B2
(45) Date of Patent: Nov. 17, 2026

(54) DEPTH GAUGE WITH MEASURING FEATURE

(71) Applicants: Smith & Nephew, Inc., Memphis, TN (US); Smith & Nephew Orthopaedics AG, Zug (CH)

(72) Inventors: Ramprasad Papannagari, Collierville, TN (US); Cassidy Burlesci-Niukkanen, Memphis, TN (US); Kyle Ritz, Milwaukee, WI (US)

(73) Assignees: SMITH & NEPHEW, INC., Memphis, TN (US); SMITH & NEPHEW ORTHOPAEDICS AG, Zug (CH)

( * ) Notice: Subject to any disclaimer, the term of this patent is extended or adjusted under 35 U.S.C. 154(b) by 0 days.

(21) Appl. No.: 18/768,420

(22) Filed: Jul. 10, 2024

(65) Prior Publication Data

US 2025/0017602 A1 Jan. 16, 2025

Related U.S. Application Data

(60) Provisional application No. 63/526,512, filed on Jul. 13, 2023.

(51) Int. Cl.

| | |
|---|---|
| ***A61B 17/17*** | (2006.01) |
| ***A61B 5/15*** | (2006.01) |
| ***A61B 17/16*** | (2006.01) |
| ***A61B 17/34*** | (2006.01) |
| ***A61B 17/70*** | (2006.01) |
| ***A61B 17/86*** | (2006.01) |
| ***A61B 90/00*** | (2016.01) |
| ***G01B 3/28*** | (2006.01) |
| ***G01B 5/18*** | (2006.01) |
| ***G01B 7/26*** | (2006.01) |
| ***G01B 11/22*** | (2006.01) |

(52) U.S. Cl.

CPC ........ *A61B 17/1728* (2013.01); *A61B 17/864* (2013.01); *A61B 5/150175* (2013.01); *A61B 17/1626* (2013.01); *A61B 17/1739* (2013.01); *A61B 17/3494* (2013.01); *A61B 17/7092* (2013.01); *A61B 2090/036* (2016.02); *A61B 90/06* (2016.02); *A61B 2090/061* (2016.02); *A61B 2090/062* (2016.02); *A61B 2090/0811* (2016.02); *G01B 3/28* (2013.01); *G01B 5/18* (2013.01); *G01B 7/26* (2013.01); *G01B 11/22* (2013.01)

(58) Field of Classification Search

CPC ... A61B 17/1728; A61B 17/864; A61B 17/17; A61B 17/1739; A61B 17/7092; A61B 17/1626; A61B 17/3494; A61B 17/58; A61B 17/00; A61B 2090/062; A61B 2090/036; A61B 2090/0811; A61B 2090/061; A61B 2562/02; A61B 90/06; A61B 5/150175; A61B 5/1076; A61B 5/4504; G01B 3/28; G01B 5/18; G01B 7/26; G01B 11/22; G01B 21/08

USPC ....... 606/916, 281, 104, 103, 86 R, 96, 102, 606/300, 87, 86 B, 915

See application file for complete search history.

(56) References Cited

U.S. PATENT DOCUMENTS

2014/0171955 A1* 6/2014 Smith ................ A61B 17/8897 606/102

* cited by examiner

*Primary Examiner* — Marcela I. Shirsat
(74) *Attorney, Agent, or Firm* — KDW Firm PLLC

(57) ABSTRACT

Depth gauges used in orthopedic surgery. Specific embodiments relate to depth gauges with a measuring feature, such as a rounded tip, intended to simulate a screw head for depth measurement during surgery.

9 Claims, 6 Drawing Sheets

DEPTH GAUGE WITH MEASURING FEATURE

This application claims the benefit of U.S. Provisional Patent Application Ser. No. 63/526,512, filed Jul. 13, 2023, and titled "Depth Gauge with Measuring Feature," the entire contents of which is hereby incorporated by reference in its entirety.

FIELD OF THE DISCLOSURE

The present disclosure relates generally to improvements to depth gauges used in orthopedic surgery. Specific embodiments relate to depth gauges with a measuring feature, such as a rounded tip, intended to simulate a screw head for depth measurement during surgery. One example described herein may be used in connection with implanting a bone plate.

BACKGROUND

Some orthopedic surgical procedures require securement of a device, such as a cannulated screw or a bone plate, to one or more bones of a patient. In some procedures, the bone plate may span one or more bones or breaks/fractures in a single bone. The bone plate may then be secured into place using one or more fasteners, such as screws. Before the bone plate is attached to the bone, an opening is typically drilled into the bone in order to accommodate the fastener. Once the opening has been prepared, the surgeon selects a fastener of the appropriate length. Selecting the appropriate length is critical because if the length is not accurate, the distal end of the fastener can extend past the drilled opening or protrude from the bone entirely. Alternatively, the head of the fastener could protrude up past the upper surface of the bone plate. Either problem can damage surrounding tissue, can prevent soft tissue from moving over the bone surface as intended, can cause pain or discomfort to the patient, or could even cause the screw head or end to pierce the skin. These complications are preferably avoided. In other examples, a cannulated screw may be positioned with respect to a hole drilled in bone. Just as with a bone plate, the head depth and position of the screw is important for proper placement. The present disclosure can help a surgeon identify where a screw would sit with respect to a bone plate and/or an opening prepared in bone.

Because the process of drilling bone does not provide an exact measurement of the depth of the bone itself, a depth gauge is commonly used to assist the surgeon in measuring the depth of the opening created. More specifically, after drilling the opening for a bone screw, the surgeon should typically measure the depth of the hole to select the appropriate length screw.

One way that surgeons help gauge the length of the screw to use is to use a probe member that can be inserted into the depth of the opening created. The probe may have graduated lengths marked therealong, much like a ruler. In other examples, the drill can be marked with calibrated bands and calibrated text size. The drill (or drill sleeve) can be marked with lines and numbers which may represent the actual opening depth and/or available screw length offerings.

An exemplary gauge is shown and described by U.S. Pat. No. 11,504,169. However, such probes do not always account for the size of the fastener head itself. They do not help the surgeon estimate or otherwise account for the shape of the fastener head that extends from the fastener shaft that will be inserted into the bone plate once the length of the fastener has been determined.

Another measuring instrument is shown and described by U.S. Pat. No. 8,936,600. This reference is a drill guide and does not consider the use of fluoroscopy during surgery in order to gauge the prominence of a fastener head. Accordingly, improvements to depth gauges and to measurement processes are thus desirable.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed are depth gauges for use in orthopedic surgery, and methods of their use. Specific embodiments relate to depth gauges with a measuring feature, such as a rounded tip, intended to simulate a fastener/screw head prominence for depth measurement during surgery. One example described herein may be used in connection with implanting a bone plate.

Further features and advantages of at least some of the disclosed embodiments, as well as the structure and operation of various embodiments, are described in detail below with reference to the accompanying drawings.

BRIEF DESCRIPTION OF THE DRAWINGS

By way of example, specific embodiments of the disclosed device will now be described, with reference to the accompanying drawings, in which.

DETAILED DESCRIPTION

Figure 1:
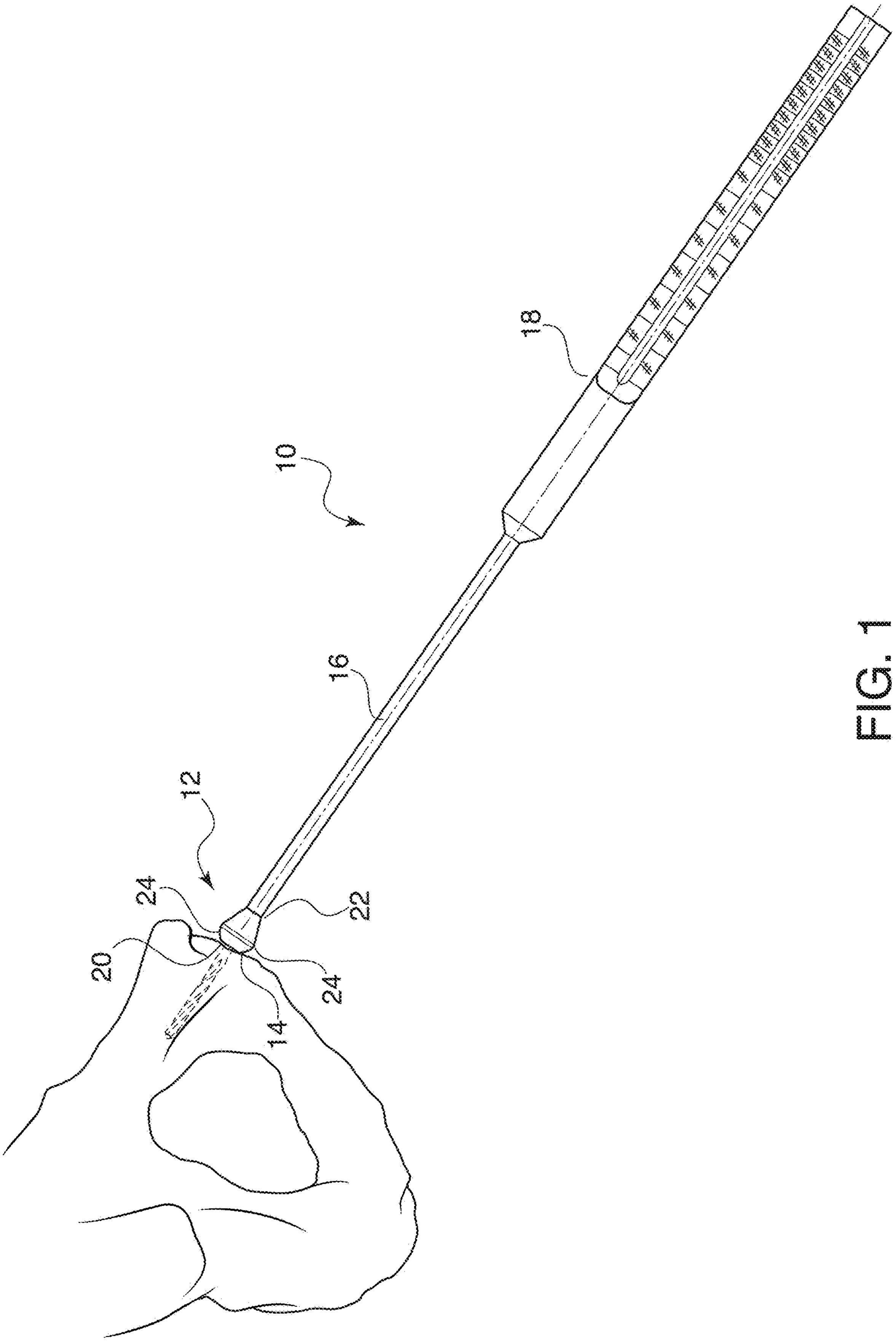
FIG. 1 shows one embodiment of a depth gauge with a measuring feature, approximating the size of a fastener head.

Various features, aspects, or the like of orthopedic instrumentation will now be described more fully hereinafter with reference to the accompanying drawing, in which one or more aspects or features of the instrumentation will be shown and described. It should be appreciated that the various features, aspects, or the like may be used independently of, or in combination, with each other. It will be appreciated that the features and instruments may be embodied in many different forms and should not be construed as being limited to the embodiments set forth herein. Rather, these embodiments are provided so that this disclosure will convey certain aspects or features of the instruments to those skilled in the art. In the drawings, like numbers refer to like elements throughout unless otherwise noted.

One embodiment of a depth gauge 10 is shown by FIG. 1. In this figure, the depth gauge 10 is shown having a distal end tip 12 with a measuring feature 14, a shaft 16, and an optional handle 18. The measuring feature 14 is shown in FIG. 1 shaped as a rounded tip, simulating the shape of a fastener/screw head. In a specific example, the measuring feature 14 will approximate the size and shape of an 8.0 mm cannulated screw head. It should be understood, however, that the measuring feature 14 may alternatively be a shaped like a flat head screw, or any other appropriate option, or any combination thereof. The general goal is that the measuring feature 14 at the distal end of the depth gauge is intended to simulate a screw head (or any other type of fastener head) shape.

The disclosed depth gauge 10 is particularly useful for verifying implant placement of bone plates that include one or more variable angle apertures for screw fixation. The depth gauge 10 can be used by positioning the (typically rounded) tip of the depth gauge in contact with the one or more variable angle apertures of the bone plate at a desired trajectory. A C-arm, x-ray, of other fluoroscopy image can be taken of the proposed position of the bone plate while the depth gauge is in contact one of the apertures. The surgeon can then visually verify from the image that the distal rounded tip does not sit proud of the bone plate, is otherwise flush, and/or that the desired/planned trajectory is acceptable.

Figure 2A:
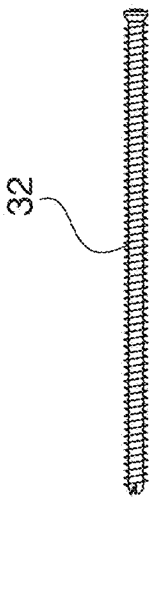
FIG. 2A shows a screw (can be a cannulated screw) that may be positioned using the present disclosure.
Figure 2B:
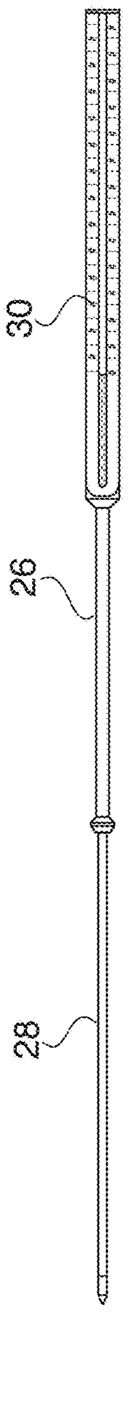
FIG. 2B shows a guide wire and a depth gauge aligned to illustrate positioning of a screw head and a depth gauge measuring feature.
Figure 2C:
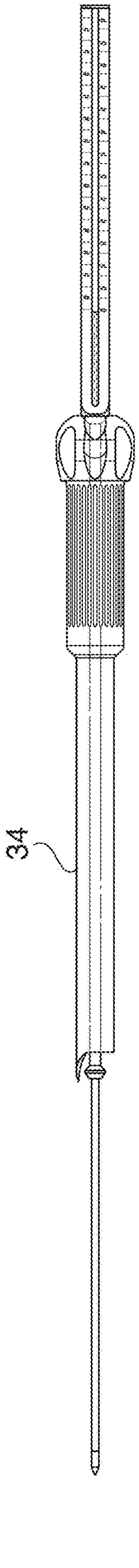
FIG. 2C shows a depth gauge inserted into a cannula.
Figure 3B:
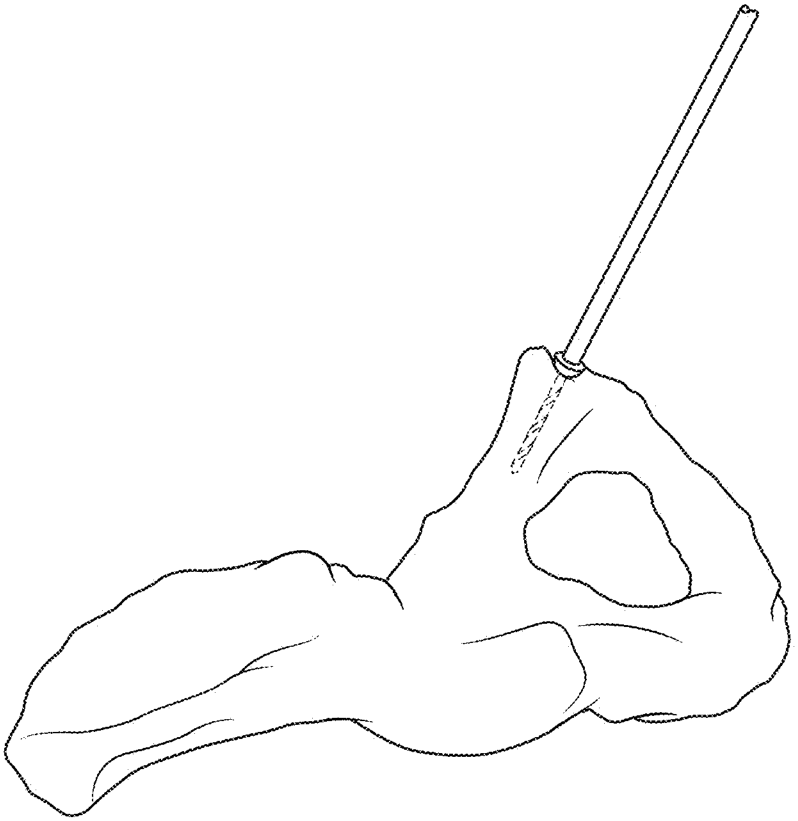
FIGS. 3A-D show a guide wire being positioned into a bone, a depth gauge being inserted over the wire for gauging the length of screw required, preparing the bone, then positioning the screw into place.
Figure 3A:
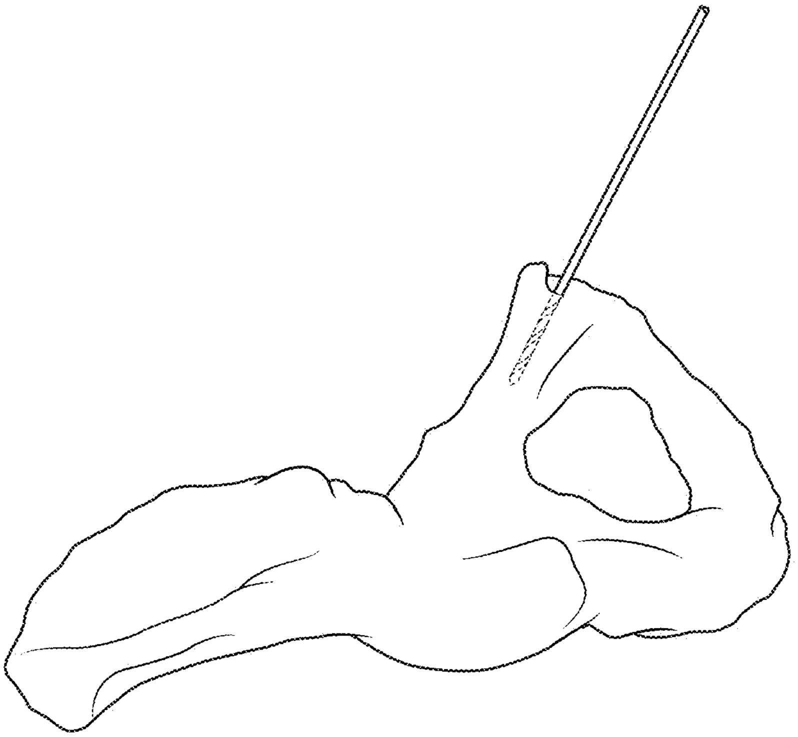
Figure 3D:
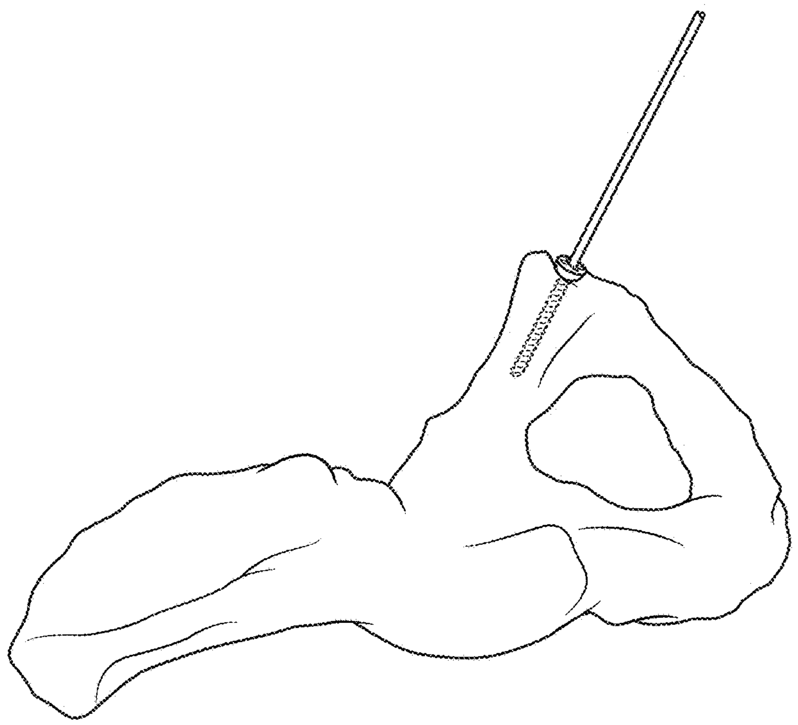
Figure 3C:
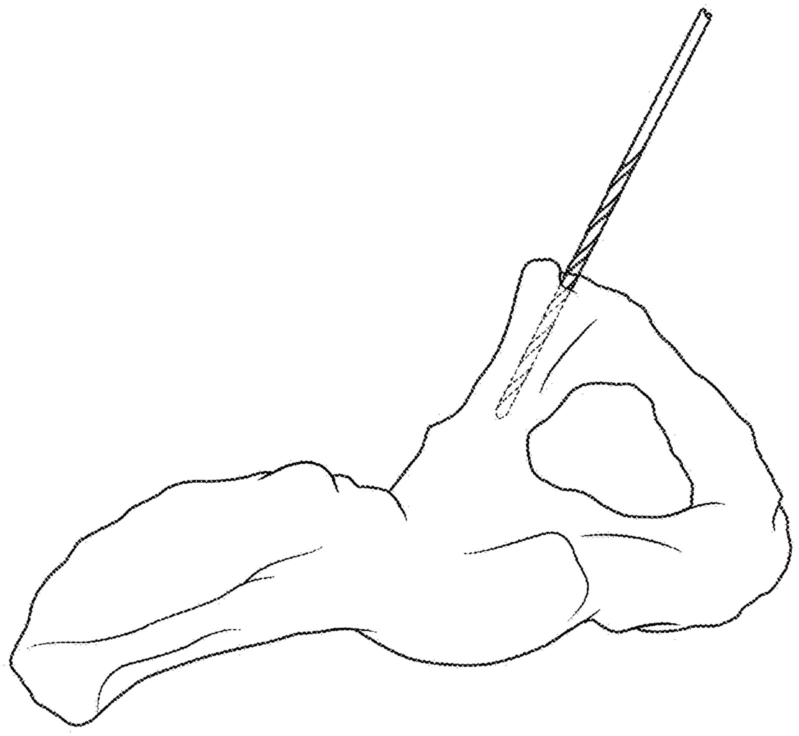

As shown by FIG. 2, in some embodiments, the depth gauge 10 may have a cannulated channel 26 running therethrough. Cannulated channel 26 allows the depth gauge to be positioned over a guide wire 28 that is positioned with respect to a bone. The handle 18 of the depth gauge may have depth markings 30 or other features. When the wire 28 is positioned with respect to bone, the depth gauge 10 can be positioned over the wire. Because the wire will generally be a fixed length, once the depth gauge 10 is positioned over the wire, the end of the wire will align with one of the depth markings 30. This can indicate the position and depth of the wire (and/or the screw) to the surgeon. In a specific example, the markings may be provided in 5 mm increments or any other appropriate increments. The distance measured may be from about 50 mm to about 180 mm, with it being understood that other measurements are possible and considered within the scope of this disclosure.

Figure 4:
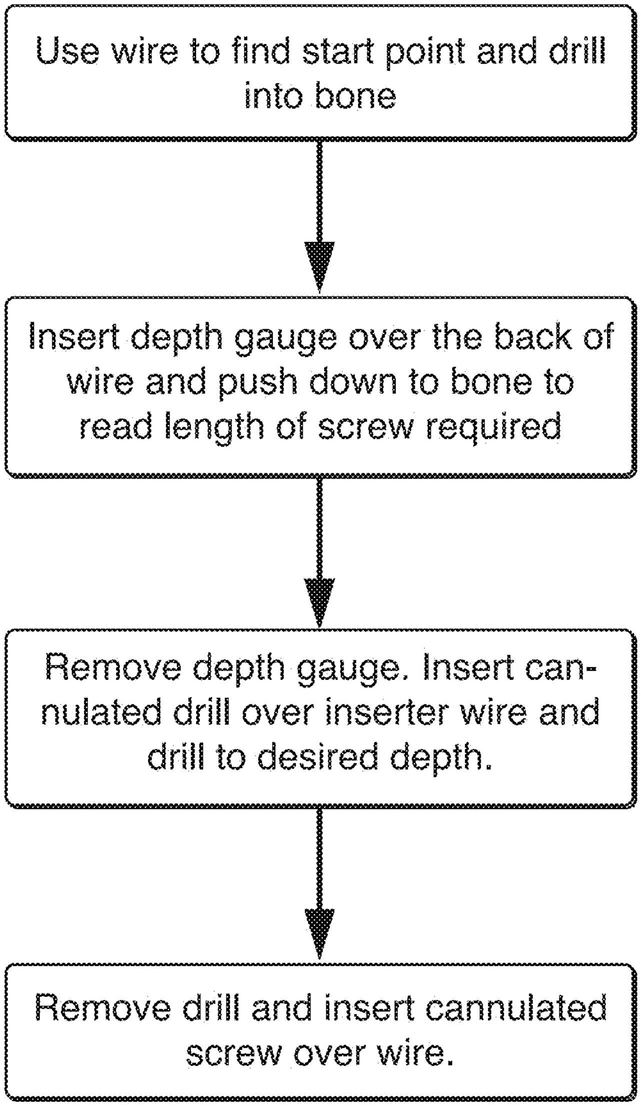
FIG. 4 is a flowchart of surgical steps that may be used for FIG. 3.
Figure 5:
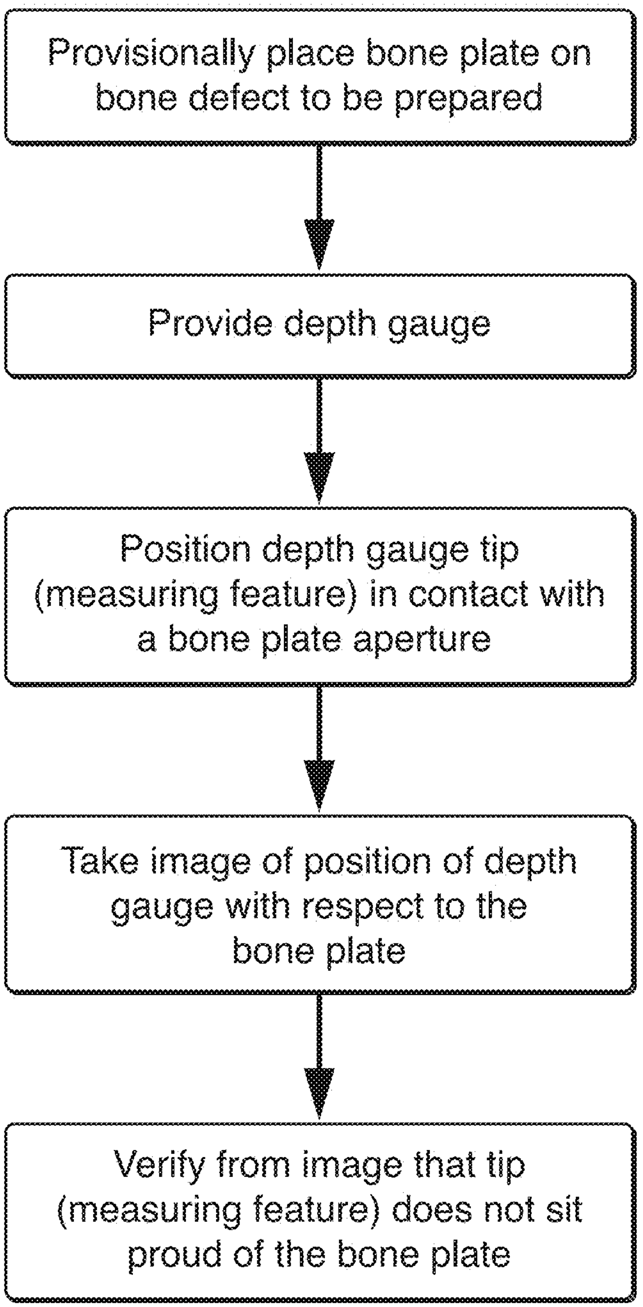
FIG. 5 shows a flowchart of surgical steps that may be used in connection with a positioning a screw with respect to a bone plate using a depth gauge having a measuring feature.

As shown by FIGS. 3 and 4, a wire may be used to identify a start point, where a screw will be drilled into bone. A depth gauge is then inserted over the back of the wire and pushed down to the bone in order to read the length of the screw required. The depth gauge is then removed and a cannulated drill is inserted over the wire. The drill is used to drill to the desired depth. The drill is then removed and a cannulated screw is inserted over the wire.

Referring back to the example shown by FIG. 1, the measuring feature 14 has a bone or plate-facing surface 20 and a shaft-facing surface 22. The bone or plate-facing surface 20 is shaped similarly to the way a fastener head is shaped at the junction between the fastener head and a fastener shaft (just without the fastener shaft in place). The shaft-facing surface 22 is shaped similarly to the way the upper head of a fastener is shaped. Because the part of the measuring feature 14 that simulates the upper curved surface of the fastener head actually contacts the shaft 16, the primary points of interest are the side surfaces 24, which will typically be outwardly curved. These can show how the fastener head will sit in the bone plate hole(s) once the correspondingly-sized fastener is inserted.

In the example shown, the measuring feature 14 is integrally formed with the shaft 16. There may be multiple depth gauges 10 provided in a kit, each depth gauge having variously-sized measuring features 14 that correspond to varying-sized fastener heads in the system. It should be understood, however, that it is also possible to provide removable depth gauge heads with variously-sized measuring features 14, with the removable heads cooperating with a single shaft 16, depending upon the different fastener head sizes that may be provided with the system components. The different removable heads could be screwed on and off of the depth gauge shaft 16. Other connection options are possible and considered within the scope of this disclosure. In an alternate embodiment, in order to minimize components of a kit, it is possible to include only a single depth gauge with a tip size that calibrates closely enough to all of the screws in the system that only one depth gauge need be used/provided.

In use, after provisionally placing the bone plate on the bone, the surgeon can place the measuring feature 14 tip in one of the plate holes at the desired screw trajectory. This can help the surgeon gauge where the correspondingly-sized fastener head will sit once the actual fastener is inserted through the bone plate and secured into the opening prepared in the bone. With the depth gauge in place, it is possible to use x-ray technology (e.g., a fluoroscopy or C arm shot) at this point in the surgery in order to confirm the position/prominence of the fastener head with respect to the bone plate, based on the depth gauge measuring feature 14 position—prior to screw insertion. If the fastener head would sit proud of the plate, adjustments can be made in either the planned trajectory of the fastener, the size of the fastener, or any other appropriate option. For example, use of the disclosed depth gauge 10 and its viewing on fluoroscopy can help show an undesirable position of the fastener head, and an alternate fastener or positioning can be selected. It is not desirable for a fastener head to sit proud of a bone plate or otherwise not be flush with the upper surface of the bone plate, because it can irritate the patient or create a myriad of other problems.

This disclosure thus provides a method of verifying implant placement. The steps may include provisionally securing a bone plate on a bone, the bone plate having one or more variable angle apertures for screw fixation, placing the measurement feature of the depth gauge in contact with one of the apertures at a desired trajectory; taking a C arm shot of the bone plate while the depth gauge is in contact with the apertures; and visually verifying from the image that the distal rounded tip of the measurement feature does not sit proud of the bone plate and the desired/planned trajectory is acceptable.

The depth gauge 10 may be provided in various lengths and thicknesses. It is envisioned that one version of the depth gauge can be sized and configured to fit through a cannula 34. This can provide for sift tissue protection. As background, when a surgeon is drilling into bone, the end of the drill can wrap fat and sinew and cause other damage, which can prevent the drill from functioning as intended. Providing a depth gauge with a length that allows it to fit through a cannula 34 can prevent soft tissue from getting wrapped around the drill or the depth gauge itself.

Changes and modifications, additions and deletions may be made to the structures and methods recited above and shown in the drawings without departing from the scope or spirit of the disclosure or the following claims.

What is claimed is:

1. A depth gauge for use with determining proper placement of a fastener head with respect to a bone plate, comprising:

a measuring feature shaped to approximate the fastener head comprising:

a plate-facing surface shaped similarly to the way the fastener head is shaped at a junction between the fastener head and a fastener shaft;

a shaft-facing surface shaped similarly to the way an upper head of the fastener head is shaped; and side surfaces disposed between the plate-facing surface and the shaft-facing surface;

wherein the sides surfaces are curved outwardly relative to the plate-facing surface and the shaft-facing surface such that a cross section parallel to and between the plate-facing surface and the shaft-facing surface comprises a diameter larger than each of a plate-facing surface diameter and a shaft-facing surface diameter and configured to be positioned within an aperture of the bone plate.

2. The depth gauge of claim 1, wherein the measuring feature comprises a distal rounded tip at the end of a shaft.

3. The depth gauge of claim 2, wherein the distal rounded tip and the shaft are integrally formed.

4. The depth gauge of claim 2, wherein the distal rounded tip and the shaft are removable from one another to provide a kit comprising multiple measuring feature options.

5. The depth gauge of claim 2, wherein the shaft forms or cooperates with a handle that comprises size or measurement markings.

6. The depth gauge of claim 1, wherein the measuring feature comprises an upper curved surface that contacts the shaft.

7. A method of measuring a screw depth, comprising:

inserting a guide wire in bone at a defined bone location;

inserting a depth gauge comprising a measuring feature shaped to approximate a screw head over the guide wire and identifying a length of a screw for use at the bone location;

removing the depth gauge and inserting a canulated drill over the guide wire to prepare bone to a desired depth;

removing the drill and inserting a cannulated screw over the guide wire, wherein the measuring feature comprises:

a bone-facing surface shaped similarly to the way the screw head is shaped at a junction between the screw head and a screw shaft;

a shaft-facing surface shaped similarly to the way an upper head of the screw head is shaped; and side surfaces disposed between the bone-facing surface and the shaft-facing surface, the sides surfaces curved outwardly relative to the bone-facing surface and the shaft-facing surface such that a cross section parallel to and between the plate-facing surface and the shaft-facing surface comprises a diameter larger than each of a plate-facing surface diameter and a shaft-facing surface diameter.

8. The method of claim 7, wherein the measuring feature of the depth gauge comprises a distal rounded tip at the end of the screw shaft.

9. A method of verifying implant placement using a depth gauge with a measuring feature, comprising:

(a) provisionally securing a bone plate on a bone, the bone plate having one or more variable angle apertures for screw fixation, (b) placing the measuring feature of the depth gauge in contact with one of the apertures at a desired trajectory;

(c) taking an image of the bone plate while the depth gauge is in contact with the aperture; and (d) visually verifying from the image that the measuring feature does not sit proud of the bone plate and that the desired/planned trajectory is acceptable;

wherein the measuring feature comprises:

a plate-facing surface shaped similarly to the way a screw head is shaped at a junction between the screw head and a screw shaft, a shaft-facing surface shaped similarly to the way an upper head of the screw head is shaped, and side surfaces disposed between the plate-facing surface and the shaft-facing surface, the sides surfaces curved outwardly relative to the plate-facing surface and the shaft-facing surface such that a cross section parallel to and between the plate-facing surface and the shaft-facing surface comprises a diameter larger than each of a plate-facing surface diameter and a shaft-facing surface diameter and configured to be positioned within the one of the apertures of the bone plate.

* * * * *